(12) United States Patent
Cong et al.

(10) Patent No.: US 8,699,766 B2
(45) Date of Patent: Apr. 15, 2014

(54) METHOD AND APPARATUS FOR EXTRACTING AND MEASURING OBJECT OF INTEREST FROM AN IMAGE

(75) Inventors: Longfei Cong, Shenzhen (CN); Yu Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 826 days.

(21) Appl. No.: 12/909,749

(22) Filed: Oct. 21, 2010

(65) Prior Publication Data

US 2011/0158490 A1 Jun. 30, 2011

(30) Foreign Application Priority Data

Dec. 31, 2009 (CN) .......................... 2009 1 0263769

(51) Int. Cl.
*G06K 9/00* (2006.01)
*G06K 9/34* (2006.01)
*G06K 9/48* (2006.01)

(52) U.S. Cl.
USPC ........................... 382/128; 382/180; 382/199

(58) Field of Classification Search
USPC .................................. 382/195, 128, 180, 199
See application file for complete search history.

(56) References Cited

U.S. PATENT DOCUMENTS

| | | | |
|---|---|---|---|
| 6,346,079 B1 | 2/2002 | Haider et al. | |
| 7,289,653 B2 * | 10/2007 | Zhang et al. | 382/131 |
| 7,634,123 B2 * | 12/2009 | Florin et al. | 382/128 |
| 7,925,064 B2 * | 4/2011 | Cloutier et al. | 382/128 |
| 7,949,474 B2 * | 5/2011 | Callahan et al. | 702/19 |
| 8,031,919 B2 * | 10/2011 | Eskildsen et al. | 382/128 |
| 8,073,226 B2 * | 12/2011 | Farag et al. | 382/131 |
| 8,320,665 B2 * | 11/2012 | Puneet et al. | 382/164 |
| 8,391,579 B2 * | 3/2013 | Barbu et al. | 382/131 |
| 2003/0099397 A1 * | 5/2003 | Matsugu et al. | 382/173 |
| 2003/0174889 A1 * | 9/2003 | Comaniciu et al. | 382/173 |
| 2005/0100208 A1 * | 5/2005 | Suzuki et al. | 382/157 |
| 2005/0238215 A1 * | 10/2005 | Jolly et al. | 382/128 |
| 2005/0254697 A1 * | 11/2005 | Zhang et al. | 382/131 |
| 2008/0002870 A1 * | 1/2008 | Farag et al. | 382/128 |
| 2008/0037875 A1 * | 2/2008 | Kim et al. | 382/199 |
| 2008/0240526 A1 * | 10/2008 | Suri et al. | 382/128 |
| 2009/0245638 A1 * | 10/2009 | Collier et al. | 382/173 |
| 2009/0252395 A1 * | 10/2009 | Chan et al. | 382/131 |
| 2010/0074507 A1 * | 3/2010 | Klottrup et al. | 382/133 |

(Continued)

FOREIGN PATENT DOCUMENTS

| | | |
|---|---|---|
| CN | 1870006 A | 11/2006 |
| CN | 101129267 A | 2/2008 |

(Continued)

OTHER PUBLICATIONS

Li et al, "Computer-aided diagnostic scheme for lung nodule detection in digital chest radiographs by use of a multiple-template matching technique", 2001, Am. Assoc. Phys Med, pp. 2070-2076.*

(Continued)

*Primary Examiner* — Kathleen Y Dulaney
(74) *Attorney, Agent, or Firm* — Kory D. Christensen; Stoel Rives LLP

(57) ABSTRACT

A method and an apparatus for extracting an object of interest from an image and measuring parameters of the object of interest are provided.

20 Claims, 5 Drawing Sheets

(56) References Cited

U.S. PATENT DOCUMENTS

| | | | |
|---|---|---|---|
| 2010/0104186 A1* | 4/2010 | Grady et al. | 382/173 |
| 2011/0026785 A1* | 2/2011 | Dewaele et al. | 382/128 |
| 2011/0026788 A1* | 2/2011 | Elter et al. | 382/128 |
| 2011/0255761 A1* | 10/2011 | O'Dell et al. | 382/131 |
| 2012/0184843 A1* | 7/2012 | Kao et al. | 600/419 |

FOREIGN PATENT DOCUMENTS

| | | |
|---|---|---|
| CN | 101161204 A | 4/2008 |
| CN | 101527047 A | 9/2009 |
| EP | 0817495 B1 | 12/2005 |

OTHER PUBLICATIONS

Hanna et al., "Automated Measurements in Obstetric Ultrasound Images", 1997, pp. 504-507, IEEE, Scientific Ultrasound Center, Cairo, Egypt, Dept. of Biomedical Engineering, Cairo University, Egypt.

Thomas et al., "Automatic Segmentation of Ultrasound Images Using Morphological Operators", IEEE Transactions on Medical Imaging, Jun. 1991, pp. 12-20, vol. 10, No. 2, IEEE.

* cited by examiner

METHOD AND APPARATUS FOR EXTRACTING AND MEASURING OBJECT OF INTEREST FROM AN IMAGE

CROSS-REFERENCE TO RELATED APPLICATIONS

This application claims the benefit of Chinese Patent Application No. 200910263769.1, filed Dec. 31, 2009, which is incorporated herein by specific reference.

TECHNICAL FIELD

The present disclosure relates to image processing.

SUMMARY

Disclosed herein are a method and apparatus for extracting and measuring an object of interest from an image in a medical imaging system.

DETAILED DESCRIPTION

Figure 1:
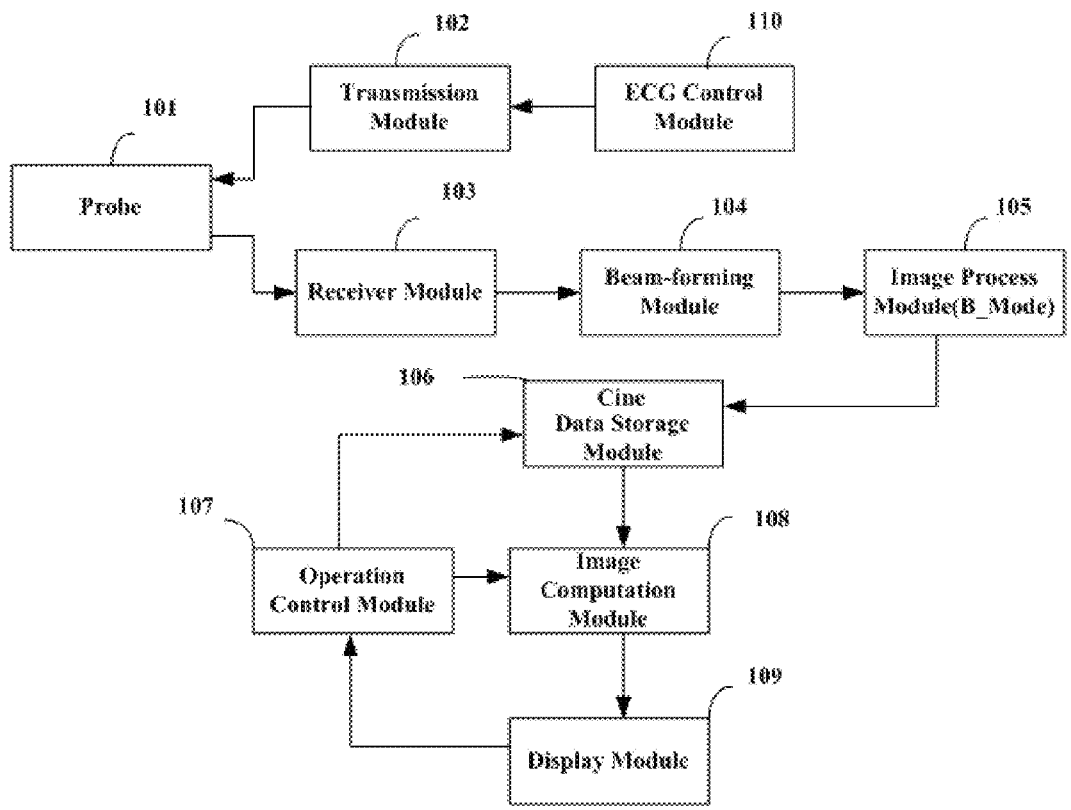
FIG. 1 is a block diagram schematically illustrating a fetal automatic measurement system.
Figure 2:
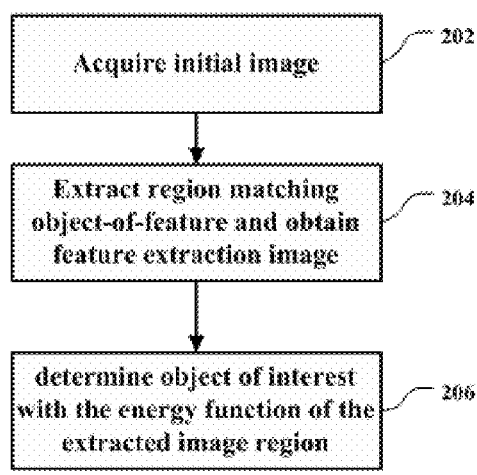
FIG. 2 is a flow diagram schematically illustrating extracting an object of interest from an image.

Fetal ultrasound measurements are one of the most important factors for estimating the condition of fetal growth and screening fetus abnormalities. Estimating fetal weight (fetal age) accurately is important for the diagnosis of giant infants and intrauterine fetal growth retardation, as well as selection of the mode of delivery. Conventionally, clinical measurement of the height and width of the uterus and the abdominal perimeter of pregnant woman has been the usual method of estimating fetal weight. With the increased availability of ultrasound technology, some fetal parameters have been measured with ultrasound and corresponding formulas have been established to predict fetal weight using a regression method. At present, the method to predict fetal weight (between 21 weeks of pregnancy and delivery) is to measure the parameters of Biparietal Diameter (BDP), Head Circumference (HC), Abdominal Circumference (AC), Femur Length (FL), etc. The fetal weight and fetal age can be estimated by measuring these parameters. Furthermore, these parameters are measured many times so as to monitor the condition of fetal growth during the period between 21 weeks of pregnancy and delivery. Taking advantage of computer image processing technology to automatically process and analyze ultrasonic images of fetuses can avoid repeated manual survey operations and improve doctors' working efficiency.

Some progress on methods of automatic measuring of head circumference has been made. The most popular method is fetal head ellipse detection based on the Hough transform or random Hough transform, which require a great deal of computation and depends on image quality and the location of fetal bone.

The present disclosure includes a method and apparatus for extracting an object of interest and measuring parameters of the object of interest with less computation and high accuracy. A method for extracting an object of interest from an image may include acquiring an initial image which contains an object of interest. The method may further include, in accordance with one or more given primary features of the object of interest, extracting one or more feature regions which match the one or more primary features to obtain a feature extraction image. The method may also include respectively computing the energy function of each of the feature regions or combinations of the feature regions, and taking the feature region whose energy function is the extreme value as the object of interest.

One embodiment of the present disclosure also comprises a method for measuring an object of interest from an image including acquiring an initial image which contains object of interest. The method may also include, in accordance with one or more given primary features of the object of interest, extracting one or more feature regions which match the one or more primary features to obtain a feature extraction image. The method may additionally include respectively computing the energy function of each of the feature regions or combinations of the feature regions and taking the feature region whose energy function is the extreme value as the object of interest. The method may also include measuring parameters of objects of interest in accordance with the determined object of interest.

One embodiment of the present disclosure also comprises an apparatus for extracting an object of interest from an image including an image acquisition module configured to acquire an initial image which contains object of interest. The apparatus may further include a feature extraction module configured for extracting, in accordance with one or more given primary features of the object of interest, one or more feature regions which match the one or more primary features to obtain a feature extraction image. The apparatus may also include an object-of-interest determination module configured to respectively compute the energy function of each of the feature regions or combinations of the feature regions, and take the feature region whose energy function is the extreme value as the object of interest.

One embodiment also comprises an apparatus for measuring an object of interest from an image including an image acquisition module configured to acquire an initial image which contains object of interest. The apparatus may also include a feature extraction module configured to extract, in accordance with one or more given primary features of the object of interest, one or more feature regions which match the one or more primary features to obtain a feature extraction image. The apparatus may further include an object-of-interest determination module configured to respectively compute the energy function of each of the feature regions or combinations of the feature regions, and take the feature region whose energy function is the extreme value as the object of interest. The apparatus may also include a measurement module configured to measure parameters of the object of interest in accordance with the determined object of interest.

The above described techniques reduce the number of candidate objects needed to be calculated. Thus, computation can be reduced and the accuracy of extracting and measuring an object of interest can be improved.

As previously noted, fetal head circumference and femur length are two important indices for estimating fetal growth. The most basic steps for detecting and screening fetal growth include acquiring a two-dimensional ultrasonic image of the fetus with a designated scanning position and measuring the fetal head circumference, femur length, etc. By adopting a method for measuring parameters of the object of interest from an image as described herein, indices of fetal head circumference, femur length, and etc. can be automatically acquired. By combining these indices with existing statistics of fetal growth, the gestational week and fetal weight can be estimated. With automatic measurement, doctors' working efficiency can be improved and the time for scanning pregnant women can be reduced.

As shown in FIG. 1, a fetal automatic measurement system may include a transmission module 102 that emits ultrasonic waves to the corresponding examination parts of human body (the abdomen of the pregnant woman) with an ultrasonic probe (or transducer) 101. The image scanning process may be triggered and controlled by the ECG signals from an ECG control module (not shown). The system may further include a receiver module 103 that receives echo signals. After being processed by a beam-forming module 104, the received echo signals are sent to an image process module 105 to acquire the gray image of the anatomic structures of the target (fetus). The image data are then stored in the cine data storage module 106. An image computation module 108 reads the image data from the cine data storage module 106, recognizing the object of interest and calculating parameters. The obtained object-of-interest information and parameters are sent to the display module 109 for user viewing. Manual operation of the system may be provided by the operation control module 107, which is used to adjust the computing result or choose the image to process.

In one embodiment, in order to measure the head circumference or femur length, the region of the fetal head or femur is initially extracted from the image by the image computation module 108, and the parameters of the fetal head circumference, biparietal diameter, femur length, and etc. may be calculated with the extracted region of the fetal head or femur. The region of the fetal head circumference or femur in the image to be measured is referred to herein as the "object of interest." it will be understood by a skilled artisan that the "object of interest" herein is not limited to the region of head circumstance or femur.

In one embodiment, a method of extracting an object of interest from an image, as shown in FIG. 1, includes an initial image acquisition step 202, a feature extraction step 204, and an object of interest determination step 206. In the image acquisition step 202, the gray images of the fetal anatomic structures, which contain the image of fetal head or femur (i.e., object of interest) are read from the cine data storage module 106. The object of interest in the initial image contains its own features which can be utilized to extract object of interest, such as luminance, morphology, location, parameters statistics, and etc.

Figure 3:
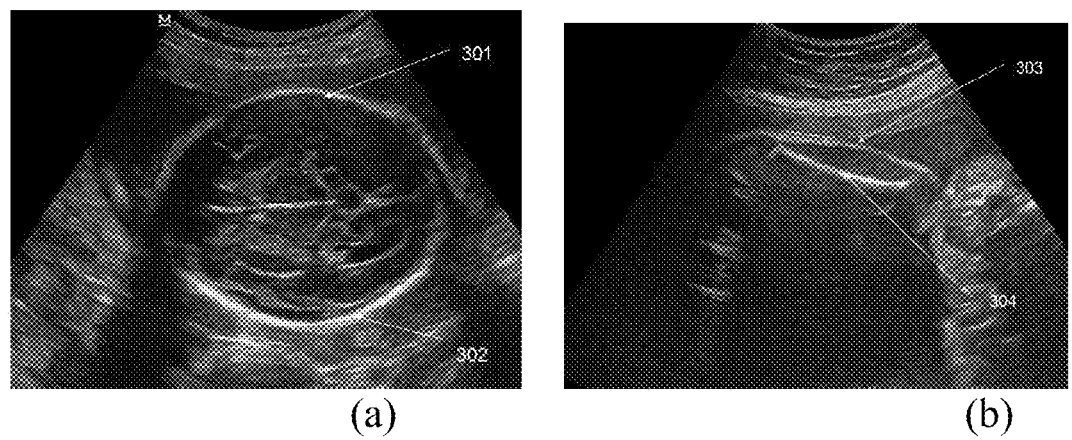
FIG. 3 is an initial image.

In the feature extraction step 204, one or more features of the object of interest can be extracted. The features utilized in the feature extraction step 204 are referred to herein as "the primary features." Examples of initial images are shown in FIG. 3, in which the image of fetal head circumference is shown in FIG. 3(a) and the image of fetal femur is shown in FIG. 3(b). In the image of fetal head circumference, the fetal head region is usually divided into two regions, the upper region (301) and the lower region (302). Therefore, the conventional method of edge detection and object recognition is inefficient in detecting objects. Thus, the head circumference can be detected and extracted with morphological features of fetal skull in image. As shown in FIG. 3, the skeleton is a continuously elongated highlighting area in the transverse direction in the image. Thus, the region of skull or femur can be detected and extracted from the image according to the luminance feature. It will be understood by a skilled artisan that the features used to extract the object of interest are not limited to the aforesaid luminance feature or morphological feature. They depend on practical conditions and can be selected based on different objects of interest.

In one embodiment, the feature extraction step 204 may include the following steps.

In accordance with the primary features of the object of interest, selecting the templates for extracting the feature regions which match the primary feature; and Processing the initial image with the templates to acquire the feature extraction image which contains the feature region matching the aforesaid features.

The skeleton shown in the FIG. 3 is a continuously elongated highlighting region in transverse direction. Under such a condition, in one embodiment, all regions with high intensity in the middle and low intensity at the upper side and lower side can be extracted and be regarded as the feature regions. The template shown in FIG. 4 can be utilized to process the initial image, that is, for every point in the initial image, the method may calculate the average intensity of the three regions respectively, multiplying the average intensity of the middle region by two, and then subtracting the average intensity of the upper region and the lower region. Thus, the result is the intensity of the point.

Each one of the three regions in the template is $R_1 \times R_5$, size rectangle, wherein the value of $R_1$ and $R_5$ can be adjusted in accordance with actual situation (such as, 10×5 pixel, or 2 mm×1 mm, etc.). After every point of the initial image has been calculated with the aforesaid method, an image can be acquired and regarded as the feature extraction image. There may be many feature regions which match the primary features of the object of interest in the feature extraction image.

Figure 4:
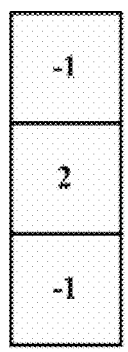
FIG. 4 is a diagram schematically illustrating a template of feature extraction.
Figure 5:
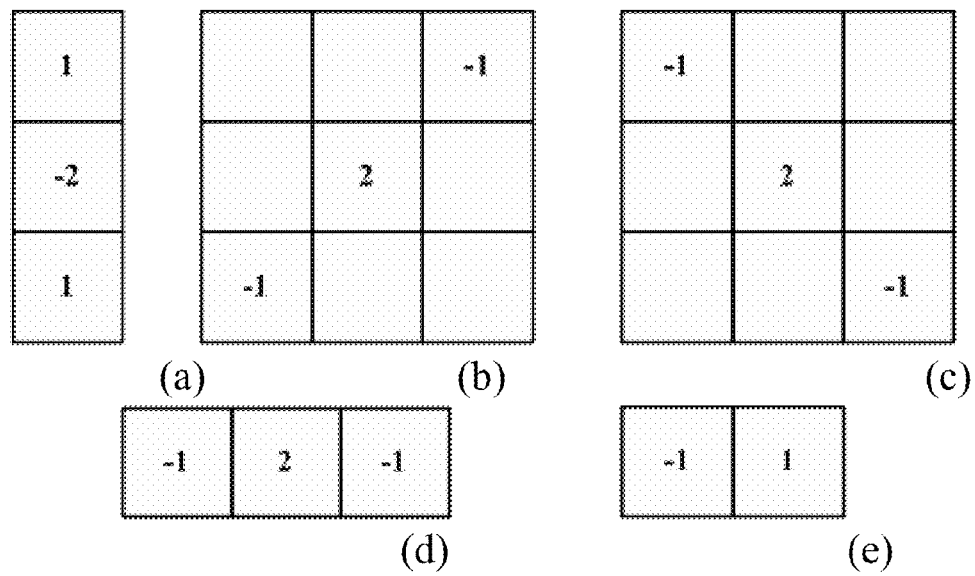
FIG. 5 is a diagram schematically illustrating other templates of feature extraction.

It can be understood by those skilled in the art that the template used to extract features is not limited to the one shown in FIG. 4. Instead, the template can be selected in accordance with the primary features of the object of interest. For example, the templates shown in FIG. 5 can be selected, or the templates which can be used to extract the feature regions matching the primary features but not shown in FIG. 4 and FIG. 5, can be selected.

The object of interest is determined from the feature regions obtained in the feature extraction step 204. These objects can be judged with the energy function of the aforesaid feature regions in the initial image. The judging process may include the steps of defining the energy function, calculating the corresponding energy function of each feature region, and comparing these energy functions. The energy function of a feature region which satisfies with given conditions is determined to be the object of interest.

In the object-of-interest determination step 206, the energy function of each feature region in the feature extraction image is initially calculated. The energy function of the feature region therein can be defined according to various requirements, such as:

the sum of the intensity of the points in the feature region of the initial image;

the sum of the intensity of the points in the feature region of the feature extraction image;

the intensity distribution assumption based on the initial image; or the joint probability of the intensity in the feature regions, etc.

In one embodiment, the energy function of each feature region is defined as the sum of the intensity of the points in the feature region of the initial image.

To reduce computation, when calculating the energy function of the feature region, instead of calculating the sum of intensity of all points, the sum of intensity of sample points sampled from the feature region may be calculated and regarded as the energy function. Taking $f_j(x_i)$, i=0, ... N as the sample of the feature region, $g(f_j(x_i))$ as the intensity of the ith sample point of the jth feature region, the energy function of the jth feature region is:

$$E_j = \sum_{i=0}^{N} g(f_j(x_i)) \quad (1)$$

After the energy functions of the feature region obtained, the object of interest can be chosen from the feature regions according to the energy functions. A judging condition can be set herein, and the feature region whose energy function satisfies the judging condition can be regard as the object of interest. The judging condition can be set in accordance with the definition of the energy function. For example, the judging condition can be the extreme value of the energy function and the feature region whose energy function is the extreme value (the maximum or the minimum) is the object of interest.

For example, in the aforesaid embodiments, the feature region whose energy function is the largest in all of the feature regions j=0, ... M is the object of interest.

The feature extraction images containing feature regions obtained in the feature extraction step 204 also contain noise and false object regions. In one embodiment, a screening step is added after the feature extraction step 204. A screening condition may be set to remove those feature regions which fail to satisfy the screening condition and retain those which satisfy the screening condition. The screening condition can be a given threshold, and those feature regions therein whose area is larger than the threshold may be retained and the rest removed. Alternatively, the screening condition may sort the areas of the feature regions, and the feature regions whose areas are larger than a particular threshold may be retained and the rest removed. For example, a method of region growing based on region connectivity can be adopted, wherein the several connected regions (e.g., the maximum six connective regions) with larger areas in the feature extraction images can be regarded as the feature regions of candidate object of interest and the rest of the regions are reverted to zero.

In the aforesaid embodiments, a de-noising step for removing noise in the feature extraction image can be added before screening step. For example, the mean $G_{mean}$ of all non-zero points in the whole feature extraction image can be selected as a threshold, and those whose data is smaller than $G_{mean}$ in the feature extraction image is set to be zero as noise.

Figure 6:
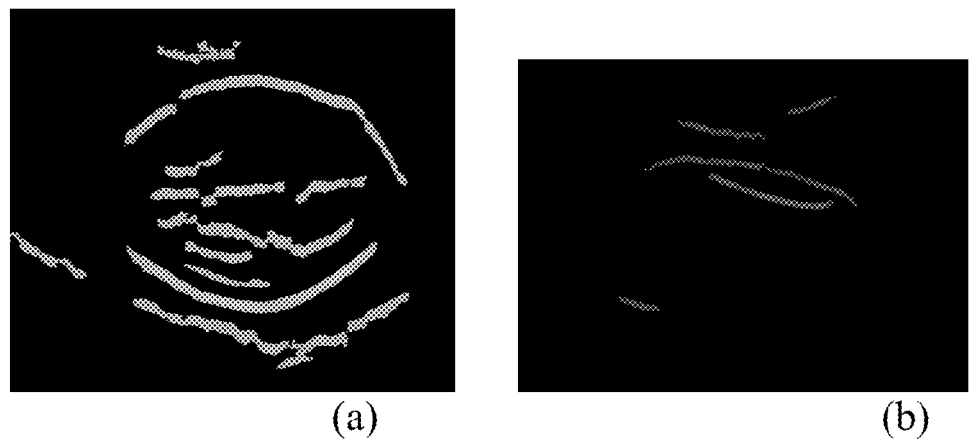
FIG. 6 is a feature image which is acquired by processing the initial image shown in FIG. 3 with a feature extraction step, a de-noising step, and screening step.

As shown in FIG. 6, (a) is the feature extraction image obtained by processing the image (a) shown in FIG. 3 with feature extraction step, de-noising step, and screening step (the feature extraction image which is obtained by such process is marked as $I_{feature}$), (b) is the feature extraction image obtained by processing the image shown in FIG. 3 (*b*) in FIG. 3 with feature extraction step, de-noising step, and screening step (that is, the $I_{feature}$ of the image (b) in FIG. 3).

In one embodiment, a candidate object extraction step can be added between the feature extraction step and object-of-interest determination step. In the candidate object extraction step, the feature regions in the aforesaid feature extraction image are further processed to extract candidate objects in accordance with the requirement of measuring an object of interest. In the object-of-interest determination step, the energy functions of candidate objects are calculated and judged so as to select the candidate objects whose energy functions are extreme values as the object of interest. In this way, there is no need to calculate all feature regions and subsequent measurement of the parameters of the object of interest can be more convenient.

In one embodiment, a thinning step can be added in the candidate object extraction step. In the thinning step, a connected region thinning algorithm (e.g., OPTA algorithm) is utilized to extract the skeleton of each of the feature regions. These skeletons are the center lines of the feature regions in the extraction feature image. The subsequent steps of energy function calculation and object of interest determination are based on these skeletons. Thus, when calculating the energy functions, instead of considering the intensity of all points in the feature regions, only the intensity of points on the skeletons or the intensity of sampling points on the skeletons are needed to be considered. In this manner, the calculation complexity can be reduced. Furthermore, if the parameters to be calculated are head circumference, abdominal circumference, or femur length, the skeleton obtained by thinning facilitates subsequent calculation of parameters of the object of interest.

Figure 7:
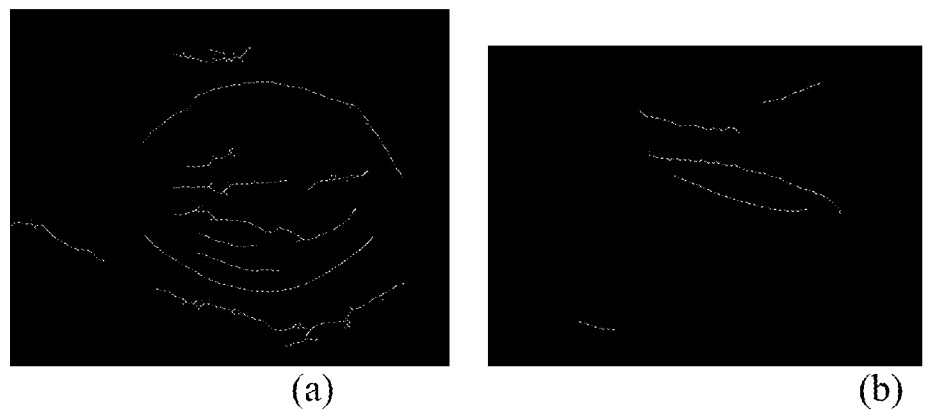
FIG. 7 is an image acquired by processing the feature image shown in FIG. 6 with an image thinning step.

As shown in FIG. 7, (a) is the image obtained by thinning the figure (a) in FIG. 6, and (b) is the image obtained by thinning the figure (b) in the FIG. 6.

If the object of interest is the femur, as the femur itself is a line, the skeleton of each feature region can be candidate for the femur. If the object of interest is the skull, as the shape of the skull is an ellipse, two departed feature regions will be obtained after the feature extraction. Thus, a further process may be needed for subsequent energy function calculation and object-of-interest determination.

Therefore, in one embodiment, a fitting step can be added after the skeleton image is obtained in the thinning step of the candidate object extraction steps. In the fitting step, the aforesaid thinned feature region (or skeleton) can be fitted to make a better extraction of the feature region in accordance with one or some features which match the object of interest. The features of the object-of-interest used for fitting are referred to herein as the "secondary features" of the object-of-interest. The morphology feature of the object-of-interest is used for fitting. As the shape of skull is an ellipse, the thinned skeleton can be elliptic fitted; the fitted result is used as a candidate feature region; the candidate feature region is calculated to obtain the energy function using the aforesaid methods; and the energy function is utilized to determine the object of interest. Thus, the object of interest is extracted with the intensity distribution feature and the morphological feature of the object of interest, which further simplifies the calculation and enhances the accuracy of extracting an object of interest.

Given the elliptic equation as $x^2+a\cdot x\cdot y+b\cdot y^2+c\cdot x+d\cdot y+e=0$, the coefficient of the ellipse (a,b,c,d,e) in the rectangular coordinate can be obtained based on the Least Square Fitting. Examining the obtained coefficient and discarding the result if $b-a^2<0$ which means the fitted result is not an elliptic equation. As the method for fitting ellipse is common, the details will not be discussed herein.

Based on the aforesaid embodiments, a fitting result examination step can be included; that is, examining the fitted result with one or some features of the object of interest. If the fitting result meets the corresponding feature, the fitting result will be retained; otherwise, the result will be discarded. Features used to examine the fitting result are referred to herein as "the third features" of the object of interest. For example, in the aforesaid embodiments, another method is usually used in describing ellipse, e.g., elliptic center coordinate (Center_x, Center_y), elliptic long axis and short axis length (Axis_l, Axis_s), and elliptic rotation angle Angle. In one embodiment, the validity of every fitted elliptic parameter is examined with the parameter statistics of the object of interest which comprises the following conditions:

(1) based on statistics data, the short axis length is larger than 1.5 cm, that is, Axis_s>1.5 cm;

(2) based on statistics data, the ratio of the short axis and the long axis of 95% fetal data is between 0.651<Axis_s/Axis_l<0.915;

(3) simultaneously restricting the center point (Center_x, Center_y) within the valid image data range.

In one embodiment, only the ellipse which meets the above restriction conditions can be regarded as the fitted result. The search for the ellipse can be efficiently speeded up by the above restriction.

A skilled artisan will understand that the examination condition in the examination step is not limited in the aforesaid conditions shown in the above embodiment. The examination conditions are varied with different objects of interest. The examination conditions can be set according to specific prior (or known) features of the object of interest or according to the actual conditions.

In one embodiment, a weighting step can be included between the feature extraction step and object-of-interest determination step. In the weighting step, the feature extraction image, or the image $I_{feature}$ obtained by the feature extraction image processed with de-noising step and screening step, is weighted to the initial image. The energy function of a feature region is defined as the sum of the intensity of points in the feature region of the weighted image. The contrast between the feature region and the surrounding region in the initial image can be expanded by weighting the initial image with the feature extraction image or the image $I_{feature}$, thus facilitating the subsequent determination of the object of interest.

Based on the aforesaid embodiments, after determining the object of interest, an optimizing step can be included for further optimizing the obtained object of interest. For example, the fetal head circumference may need to be measured in one embodiment. After obtaining the object of interest (an ellipse in the present embodiment), for each parameter of Center_x, Center_y, Axis_l, Axis_s, Angle, a local optimized value of the energy function E can be obtained for further optimizing the elliptic parameter based on searching for a certain step (e.g. one pixel) in the neighborhood of each parameter. The energy function used in local searching herein can be the energy function in the formula (1) or the energy functions mentioned in the aforesaid embodiments. The parameter value corresponding to the extreme value (the maximum or the minimum) of the energy function is regarded as the final elliptic parameter.

In an exemplary embodiment, the femur may be taken as the object of interest, and the femur length is needed to be measured. As the two endpoints of the obtained object of interest (that is, the two endpoints of the skeleton line of femur) are usually not the exact endpoints of the femur, the positions of the two endpoints may need to be optimized. Since the skeleton line is usually longer than the actual femur length, the two endpoints of the femur may be searched only within the skeleton line. The intensity of the ultrasonic image obeys a distribution b(a,y) wherein a is the distribution parameter. For example, a Gaussian Distribution may be used in one embodiment, and a is a vector representing mean value and variance. The given positions of the two endpoints may be used to compute the intensity distribution parameter $a_1$ of the points in the image along the skeleton line between the two endpoints, and to compute the intensity distribution parameter $a_2$ of the two sides of the femur region (larger than a certain distance) and the outer side region of the given endpoint along the skeleton line. The joint probability of the points in the above two regions can be computed as the energy based on $a_1$, $a_2$, the positions where the energy is the largest as the final femur endpoints. The function b(a,y) herein can be a Gaussian Distribution, or a Rayleigh Distribution, or other distribution functions. In the depicted embodiment, the Gaussian Distribution is used to optimizing the endpoints.

Based on the aforesaid embodiments, a method for measuring parameters of the object of interest in image is provided. A measurement step can be added after the object of interest is obtained with methods mentioned in the aforesaid embodiments. Parameters of the obtained object of interest can be measured in the measurement step. For example, in one embodiment, after the head circumferential ellipse (the object of interest) is obtained, the elliptic short axis is corresponded to the fetal Biparietal Diameter, and the length of the femur (the skeleton) is corresponded to the femur length. Similarly, the three important indices of fetal clinics, e.g., fetal Biparietal Diameter, Head Circumference and the Femur Length, can be obtained.

An apparatus for extracting an object of interest from an image and measuring relevant parameters is also disclosed.

Figure 8:
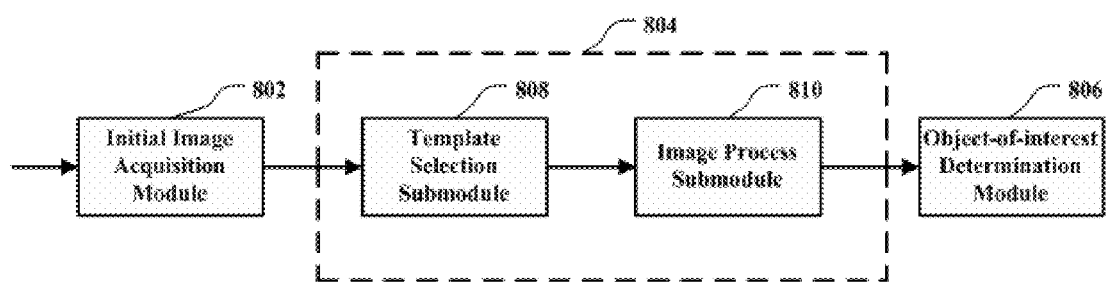
FIGS. 8 and 9 are module diagrams schematically illustrating embodiments of an apparatus for extracting an object of interest from an image.

In one embodiment, the image computation module 108 shown in the FIG. 1 comprises an apparatus for extracting an object of interest. As shown in FIG. 8, the apparatus for extracting an object of interest comprises an initial image acquisition module 802, a feature extraction module 804, and an object-of-interest determination module 806. The initial image acquisition module 802 reads an initial image from the cine data storage module 106 and sends the initial image to the feature extraction module 804. The feature extraction module 804 processes the initial image with the primary feature of the object of interest, and extracts feature regions which meet the primary feature from the initial image to obtain feature extraction image. The object-of-interest determination module 806 computes the energy function of each feature region respectively obtained by the feature extraction module 804 and compares the computed energy function of each of the feature regions to judge which energy function is the extreme value. Thereafter, the feature region whose energy function is the extreme value is regard as the object of interest.

The feature extraction module 804 may include a template selection sub-module 808 and an image processing sub-module 810. The template selection sub-module 808 selects the template used for extracting the feature region matching the primary feature in accordance with the primary feature of the object of interest. The image processing sub-module 810 processes the initial image with the selected template to acquire a feature extraction image which contains the feature region matching the primary feature.

In one embodiment, the apparatus for extracting an object of interest mentioned in the aforesaid embodiments may also include one or more of the following modules: a candidate object extraction module 805, a screening module 812, a weighting module 822, and an optimizing module 826. The screening module 812, which is in communication with the feature extraction module 804, discards the feature regions which fail to meet the screening condition from the feature extraction images obtained by the feature extraction module 804. The candidate object extraction module 805, which is in communication with the feature extraction module 804 and/or the screening module 812, extracts candidate objects from feature regions of the feature extraction image obtained by the feature extraction module 804 and/or of the feature extraction image processed by the screening module 812. The weighting module 822, which is in communication with the feature extraction module 804 and/or the filtering module 812, weights the feature extraction image, which has been processed by the feature extraction module 804 and/or the filtering module 812 to the initial image. The optimizing module 826, which is in communication with the object-of-interest determination module 806, optimizes the object of interest obtained by the object-of-image determination module.

The candidate object extraction module 805 may include one or more of the following modules: a thinning sub-module 816, a fitting sub-module 818, and an examination sub-module 820. The thinning sub-module 816, which is in communication with the feature extraction module 804 and/or the screening module 812, thins the feature regions of the feature extraction image obtained by the feature extraction module 804 and/or of the feature extraction image screened by the screening module 812. The fitting sub-module 818, which is in communication with the thinning sub-module 816, fits the feature area thinned in the sub-module 816 to obtain at least one fitted feature area according to the secondary feature of the object of interest. The examination sub-module 820, which is in communication with the thinning sub-module 816, sets an examination condition according to the third feature of the object of interest, judges the fitted feature regions with the examination condition, and discards the fitted feature regions which fail to meet the examination condition.

Figure 9:
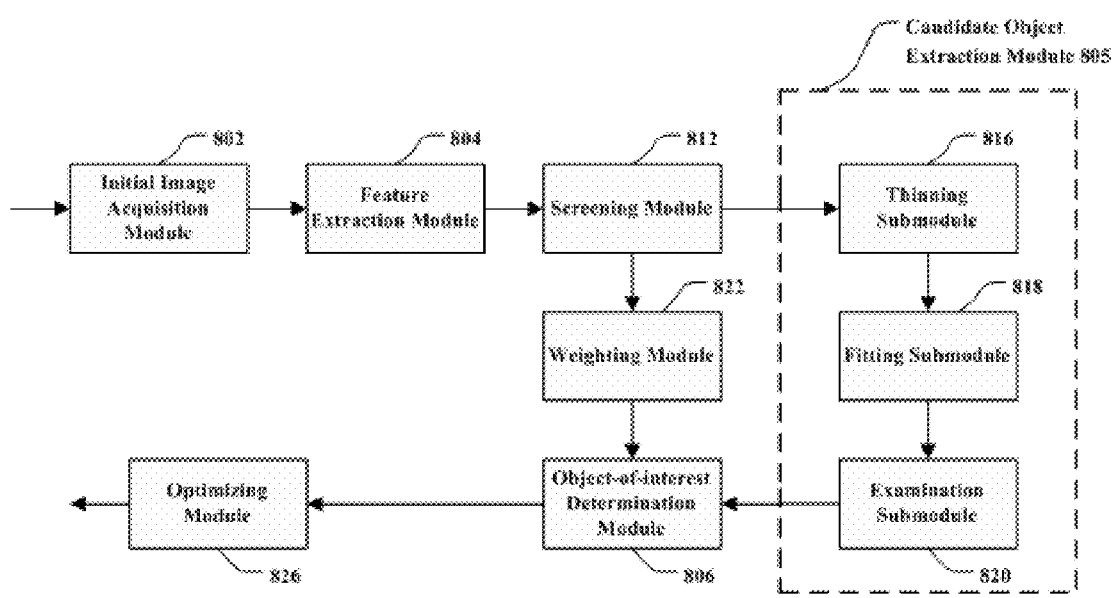

One or more modules of the filtering module 812, thinning sub-module 816, fitting sub-module 818, examination sub-module 820, weighting module 822 and optimizing module 826 may be included. As shown in FIG. 9, in one embodiment, the apparatus for extracting an object of interest includes all of the aforesaid modules.

An apparatus for measuring parameters of the object of interest in an image is provided in one embodiment. The apparatus for measuring parameters of the object of interest, which is based on the apparatus for extracting an object of interest in the aforesaid embodiments, may include a measurement module 828 which communicates with the object-of-interest determination module 806 and/or the optimizing module 826, and measures parameters of the object of interest obtained by the object of interest determination module 806 or optimized by the optimizing module 826. The structures of the other modules or sub-modules in this embodiment are identical to the corresponding modules or sub-modules in the aforesaid embodiments and will not be discussed again.

The method and the apparatus for extracting an object of interest and measuring parameters of the object of interest from an image in each embodiment of the present disclosure are not limited to being utilized in measuring fetal Head Circumference, Biparietal Diameter, and Femur Length. They can be utilized in extracting and measuring other objects, such as extracting fetal spine and facial contour from an ultrasonic image, bones (such as ribs) from X-ray image, or other objects with special shapes from other images.

While specific embodiments and applications of various methods and devices have been illustrated and described, it is to be understood that the invention claimed hereinafter is not limited to the precise configuration and components disclosed. Various modifications, changes, and variations apparent to those of skill in the art may be made in the arrangement, operation, and details of the methods and systems disclosed.

Furthermore, the methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified without departing from the scope of the invention as claimed.

The embodiments disclosed may include various steps, which may be embodied in machine-executable instructions to be executed by a general-purpose or special-purpose computer or other electronic device. Alternatively, the steps may be performed by hardware components that contain specific logic for performing the steps, or by any combination of hardware, software, and/or firmware.

Embodiments of the present invention may also be provided as a computer program product including a non-transitory machine-readable medium having stored thereon instructions that may be used to program a computer (or other electronic device) to perform processes described herein. The machine-readable medium may include, but is not limited to, floppy diskettes, optical disks, CD-ROMs, DVD-ROMs, ROMs, RAMs, EPROMs, EEPROMs, magnetic or optical cards, or other type of media/machine-readable medium suitable for storing electronic instructions.

Those of skill in the art would further appreciate that the various illustrative logical blocks, modules, circuits, and algorithm steps described in connection with the embodiments disclosed herein may be implemented as electronic hardware, computer software, or combinations of both. To illustrate the interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the invention as claimed hereinafter.

What is claimed is:

1. A method for extracting an object of interest from an image, comprising:
  acquiring an initial image containing an object of interest;
  in accordance with one or more given primary features of the object of interest, extracting one or more feature regions which match the one or more primary features to obtain a feature extraction image; and
  respectively computing an energy function of each of the feature regions or combinations of the feature regions, and taking the feature region whose energy function is the extreme value as the object of interest;
  wherein the energy function is defined as the sum of the intensities of the points in the feature regions of the initial image, and/or the sum of intensities of the points in the feature regions of the feature extraction image, and/or a joint probability of the intensity in the feature regions of the initial image.

2. The method of claim 1, wherein extracting feature regions comprises:
   in accordance with the given primary features of the object of interest, selecting a template matching the primary features; and
   processing the initial image with the template and extracting one or more feature regions which match the primary features to obtain the feature extraction image.

3. The method of claim 1, wherein at least one of the primary features of the object of interest is intensity.

4. The method of claim 1, further comprising, after extracting the one or more feature regions, removing the one or more feature regions which fail to meet a given screening condition in the feature extraction image.

5. The method of claim 1, further comprising, after extracting the one or more feature regions, extracting candidate objects from the feature regions extracted from the extraction feature image; and
   calculating the energy functions of the candidate objects, and taking the candidate objects whose energy functions are extreme values as the object of interest.

6. The method of claim 5, wherein extracting candidate objects comprises thinning the feature regions and taking one or more thinned feature regions as the candidate objects.

7. The method of claim 6, further comprising, after thinning the feature regions, fitting the thinned feature regions to obtain at least one fitted feature region in accordance with a given secondary feature of the object of interest, and taking the fitted feature regions as the candidate objects.

8. The method of claim 7, wherein the secondary feature comprises a morphological feature.

9. The method of claim 8, further comprising, after fitting the thinned feature regions, setting an examination condition in accordance with a given third feature, examining the fitted feature regions with the examination condition, and discarding the fitted feature regions which fail to meet the examination condition.

10. The method of claim 9, wherein the third feature comprises at least one parameter statistics of the object of interest.

11. The method of claim 1, further comprising, after extracting the feature regions, weighting the feature extraction image to the initial image, wherein, in the energy function, the initial image is the initial image which has been weighted.

12. The method of claim 1, further comprising optimizing the object of interest.

13. An apparatus for extracting an object of interest from an image comprising a computer including a non-transitory computer-readable medium storing program modules executable by the computer, the modules including:
   an image acquisition module configured for acquiring an initial image containing the object of interest;
   a feature extraction module configured for extracting, in accordance with one or more given primary features of the object of interest, one or more feature regions which match the one or more primary features to obtain a feature extraction image;
   an object-of-interest determination module configured for respectively computing an energy function of each of the feature regions or combinations of the feature regions, and taking the feature region whose energy function is the extreme value as the object of interest;
   a candidate object determination module configured for extracting candidate objects from the feature regions; and
   a thinning sub-module in communication with feature extraction module or screening module and configured for thinning the feature regions and taking the thinned feature region as the candidate objects.

14. The apparatus of claim 13, wherein the feature extraction module comprises:
   a template selection sub-module configured for selecting a template matching the one or more primary features; and
   an image processing sub-module configured for processing the initial image with the template to obtain the feature extraction image.

15. The apparatus of claim 13, further comprising:
   a screening module in communication with the feature extraction module and configured for removing the feature regions which fail to meet a given screening condition.

16. The apparatus of claim 13, further comprising:
   a fitting sub-module in communication with the thinning sub-module and configured for fitting the thinned feature regions to obtain at least one fitted feature region in accordance with a given secondary feature of object of interest, and taking the fitted feature regions as the candidate objects.

17. The apparatus of claim 13, further comprising:
   an examination sub-module in communication with fitting sub-module and configured for setting an examination condition in accordance with a given third feature, examining the fitted feature regions with the examination condition, and discarding the fitted feature regions which fail to meet the examination condition.

18. The apparatus of claim 13, further comprising:
   a weighting module configured for weighting the feature extraction image to the initial image.

19. The apparatus of claim 13, further comprising:
   an optimizing module configured for optimizing the object of interest.

20. A method for extracting an object of interest from an image, comprising:
   acquiring an initial image containing an object of interest;
   in accordance with one or more given primary features of the object of interest, extracting one or more feature regions which match the one or more primary features to obtain a feature extraction image;
   respectively computing an energy function of each of the feature regions or combinations of the feature regions, and taking the feature region whose energy function is the extreme value as the object of interest;
   after extracting the one or more feature regions, extracting candidate objects from the feature regions extracted from the extraction feature image, wherein extracting candidate objects comprises thinning the feature regions and taking one or more thinned feature regions as the candidate objects; and
   calculating the energy functions of the candidate objects, and taking the candidate objects whose energy functions are extreme values as the object of interest.

* * * * *